United States Patent
Smid et al.

(10) Patent No.: US 6,709,386 B2
(45) Date of Patent: Mar. 23, 2004

(54) ENDOSCOPE FILL BAR

(75) Inventors: Frank-Michael Smid, Hamburg (DE); Michael Wiegand, Nehren/Tübingen (DE); Thomas Wosnitza, Lüneburg (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 0 days.

(21) Appl. No.: 10/242,962

(22) Filed: Sep. 13, 2002

(65) Prior Publication Data

US 2003/0073882 A1 Apr. 17, 2003

(30) Foreign Application Priority Data

Sep. 13, 2001 (DE) .......................... 101 45 107

(51) Int. Cl.⁷ ................................ A61B 1/00
(52) U.S. Cl. ............... 600/104; 604/106; 604/107; 604/170.02; 600/127
(58) Field of Search ................... 600/104, 106, 600/114, 127, 129, 138; 604/106, 107, 170.01, 170.02

(56) References Cited

U.S. PATENT DOCUMENTS

| 5,195,505 A | * | 3/1993 | Josefsen ..................... 600/204 |
| 5,649,947 A | * | 7/1997 | Auerbach et al. ............ 606/170 |
| 5,662,585 A | * | 9/1997 | Willis et al. ................. 606/104 |
| 6,030,402 A | * | 2/2000 | Thompson et al. .......... 606/185 |

FOREIGN PATENT DOCUMENTS

DE          81 19 687.3 U1      7/1981

* cited by examiner

Primary Examiner—John Mulcahy
(74) Attorney, Agent, or Firm—Rankin, Hill, Porter & Clark LLP

(57) ABSTRACT

An endoscope fill bar including a device to change the cross-section of a rounded end zone of the fill bar that protects distally beyond the endoscope distal end when the fill bar is in its functional position. The cross-sectional altering device is driven by an adjusting system mounted on the fill bar and through an adjustment link, and includes a lever resting at the distal end zone in a spreading-out and retracting manner.

8 Claims, 3 Drawing Sheets

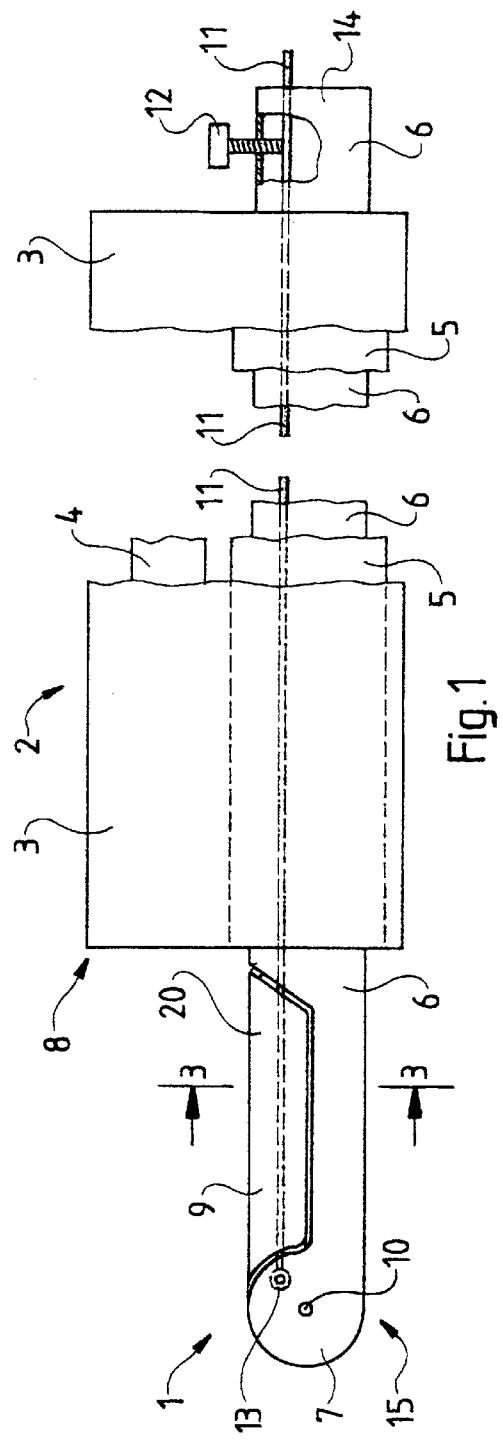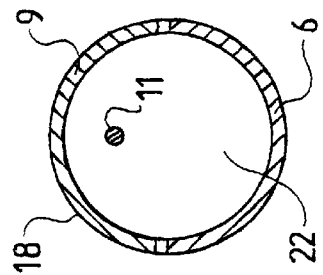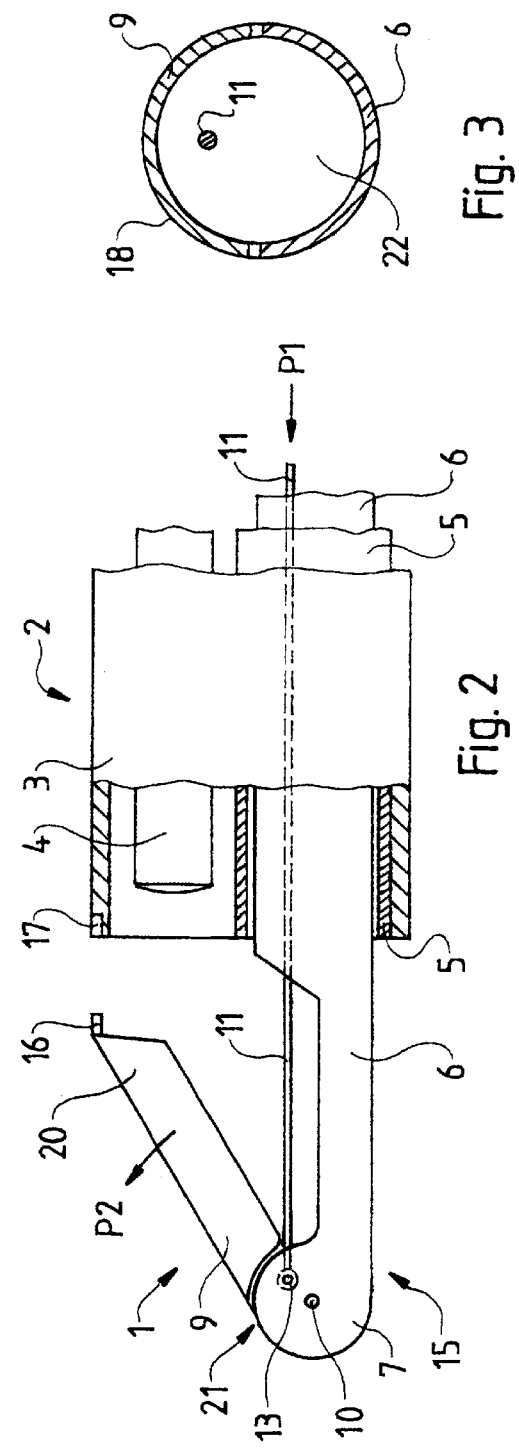

ENDOSCOPE FILL BAR

Figure 4:
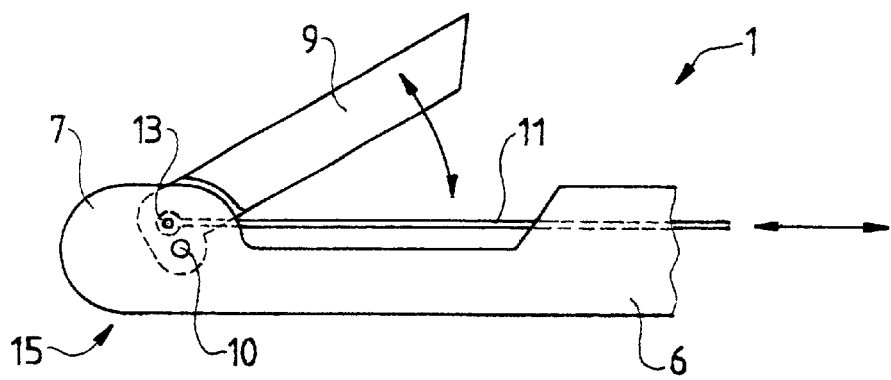

The invention relates to an endoscope fill bar as defined in th preamble of claim 1.

Endoscope are used in minimally invasive surgery and for diagnostic purpose. When used as intended, they are advanced through a body duct, which for that purpose was pierced into the patient's body, or through a natural duct of that body, and into the body cavity to be investigated. Obviously too, the insertion and advance of the endoscope should be as easy as possible and with a minimum of trauma to the body duct. At least with respect to the insertion, such minimization might be attained by rounding the distal tip of the endoscope. The endoscopes themselves however cannot be rounded permanently because having to meet different other requirements, for instance assuring good observability and illumination of the treatment region, the flow to-and-fro of rinsing fluid, or the insertion of implements.

Accordingly a fill bar is used to round the distal endoscope tip. This fill bar is inserted through a clear endoscope duct into this endoscope. When in its functional position, the fill bar runs through the entire length of the endoscope from which it projects distally by a rounded, distal zone. Once the fill bar is in position, the endoscope is moved into the body duct and advanced as far as the pertinent region of surgery. Thereupon the fill bar may be removed in the proximal direction from the endoscope and treatment may begin.

A fill bar outside the above species furthermore is known from the German patent document 81 19 687 U 1, comprising a lever resting in articulating manner on said bar's distal end so as to be adjustable at its proximal end. This lever when in its functional position may pivot in front of the distal endoscope end and must match the endoscope cross-sectionally.

When the duct receiving the fill bar being inserted into the endoscope substantially is the full endoscope cross-section, for instance the way it is with an endoscope with a detachable shank through which the fill bar may be guided, then such a fill bar shall satisfactorily round the distal endoscope tip. However there remains a slight offset between the endoscope and the fill bar which, in the above instance, substantially corresponds to the shank's wall thickness or where applicable to the thickness of the insulating inset constituted at the shank end.

But if this offset is larger, endoscope insertion in spite of the use of a fill bar still may be traumatizing.

A fill bar is known in the state of the art which is fitted with a device allowing varying the cross-section of the zone distally beyond the endoscope in its functional position. Such a fill bar of the species of the present invention illustratively is known as the Leusch expansion shutter (G. Leusch, [A smooth fill bar of beak-free resection shanks], UROLOGE A 13, 274-275-1974). This fill bar comprises two parts which are axially displaceable relative to each other and an annular soft bead in the distal end zone that may be compressed or tensioned by said relative displacement so that an offset as mentioned above between the fill bar and the endoscope may be overlapped. Stretching the bead entails a reduction of its diameter and thereby allows inserting and retracting the fill bar through the endoscope duct.

However even this improved fill bar fails if only an endoscope duct of small insertion cross-section relative to the total endoscope cross-section is available to insert the said fill bar. Such is the case for instance with wide shank implements wherein only one functional duct of substantially lower cross-section than that of the endoscope is free. As regards such implements, the distal endoscope tip heretofore could not be satisfactorily rounded using fill bars. Even the above cited expansion shutter may compensate only slight offsets. Moreover it shall always be unsuitable if the free duct used to insert the fill bar is mounted eccentrically in the endoscope, or when the endoscope itself lacks a circular cross-section. Using the heretofore known fill bars in all these instances may only partly cover, i.e. round off the tip, other bared edges remaining.

Accordingly the objective of the present invention is to create a fill bar overcoming the above described problems but allowing inserting endoscopes exhibiting the said unfavorable tip geometry into a body duct while causing only slight trauma.

This problem is solved by the invention using a fill bar defined by the features of claim 1.

Accordingly, the device to change the cross-section of the region distally projecting beyond the endoscope in the functional position of the fill bar is a pivoting lever supported in that region. By means of an appropriate and proximal adjustment element, said lever may be pivoted within the lever's pivoting range to enlarge the cross-sectional area of the fill bar. Such pivoting motion also may be reversed by said adjusting element, thus reversing the cross-sectional enlargement, and the fill bar then again may be guided through the free endoscope duct. At its distal end said lever articulates on the fill bar so that, in its pivoted position, the fill-bar cross-section increases from its distal tip and in the proximal direction over the length of this lever.

The fill bar of the invention also allows safely covering, i.e. rounding, even substantial offsets. For that purpose, the length and the pivoting angle of the lever must be selected appropriately. In particular even endoscopes comprising an eccentric fill-bar insertion duct may be reliably rounded because said lever also allows non-circular enlargement of cross-section. At the same time the present invention also is characterized by simple design and simple operability.

The lever must be supported at the fill-bar zone distally projecting beyond the endoscope in such a way that the lever shall be able to assume a state wherein the cross-section has been enlarged due to pivoting the lever and a state allowing passing the fill bar through the free endoscope duct.

Illustratively the lever may articulate on the distal end of the fill bar. However claim 2 advantageously proposes that the lever shall be mounted proximally from a distal, rounded tip of the fill bar. This distal fill-bar tip then retains unchanged its selected, closed, traumatic shape even when the lever has been pivoted, and in this manner it improves insertion of an endoscope fitted with this fill bar.

The lever geometry may be selected in arbitrary manner. However in a preferred embodiment defined in claim 3, this lever preferably shall comprise a cylindrically convex outside surface away from the fill bar because said surface shall come into contact with the body-duct tissue when the fill-bar fitted endoscope shall be inserted. Said convex cylindrical shall advantageously reduce the trauma of insertion.

Claim 4 advantageously proposes that the free lever end be designed to enable resting on the distal endoscope end. As a result the pivoted lever shall be stabilized at insertion, and gaps between the lever and the endoscope tip shall be avoided. Stability of the pivoted lever is important because significant forces are applied to said lever when the endoscope is inserted into the body duct which usually must be expanded.

In addition, or as an alternative in the event of a stable design to the step of claim 4, an affixation mechanism may be used to keep the lever in its pivoted position. Preferably as regards claim 5, the affixation mechanism shall be mounted on the adjustment system because latter can be reached outside the endoscope by the surgeon and hence the affixation mechanism shall be more easily actuated. In a simple design, such an affixation mechanism might be for instance a detachable clamping screw or a lock so that the adjustment system shall be locked. However an arbitrary detent mechanism also may be used, for instance a spring-loaded ball which upon actuation of the adjustment system shall engage corresponding grooves. The affixation mechanism shall be designed in such a way that the forces acting on the pivoted lever shall be opposed.

Moreover a spring element may be configured between the lever and the fill bar in order to facilitate pivoting the lever on one hand and on the other hand to apply a retention force on the pivoted lever to oppose the forces exerted on the lever during insertion. Said spring force shall be selected in such a way that folding the lever shall still be possible with moderate force.

Moreover the lever and the associated adjustment system besides the adjustment link may be designed in such a way that the lever may assume several pivoted positions, that is several pivot angles. Such a state on one hand might be reached by stepwise adjustments, but on the other hand it might also be carried out in continuous manner. In both cases the fill bar shall be appropriate for various sizes of offsets, also for endoscopes of various diameters.

The fill bar advantageously shall be designed so that it might reach its functional position only in one predetermined rotational position relative to its endoscope in order that the pivoting direction of the lever always shall correspond to the direction of the offset to be covered between the fill bar and the endoscope. In addition the fill bar and the endoscope shall be coupled in mutually irrotational manner in order that the fill bar shall be precluded from rotating relative to the endoscope, whereby the lever no longer would overlap optimally. This feature is especially significant for an insertion duct which is eccentric in the endoscope or with respect to an endoscope of oval cross-section.

Claim 6 advantageously proposes mounting several levers which may be pivoted in different directions. These arms then may overlap offsets in several directions in the manner of the spokes of an umbrella.

Advantageously in the above and as stated in claim 7, levers of different lengths are used. In this manner small offsets for instance may be covered in one direction with short arms and large offsets in another direction with commensurately longer arms. As regards endoscopes exhibiting oval cross-sections, the end face to be covered is not configured symmetrically with respect to the center about the insertion duct, and accordingly the above suggested length differentials of the levers result in improved overlap or rounding.

The adjustment system is advantageously designed in the manner defined in claim 8 in that, upon lever motion due to actuating the adjustment link, the free lever end essentially moves along a straight path transversely to the longitudinal axis of the fill bar. This goal may be attained by supporting the lever on a displaceable shaft. Short of such a design of the adjustment link, the pivoting motion of the lever would require a short tensive motion in the proximal direction at the fill bar in order to move the pivoted lever to rest against the distal endoscope tip or a short distal motion of the fill bar, before it would be possible to retract the lever by means of the adjustment link.

The invention is elucidated below in relation to the Figures schematically showing various embodiment modes.

Figure 5:
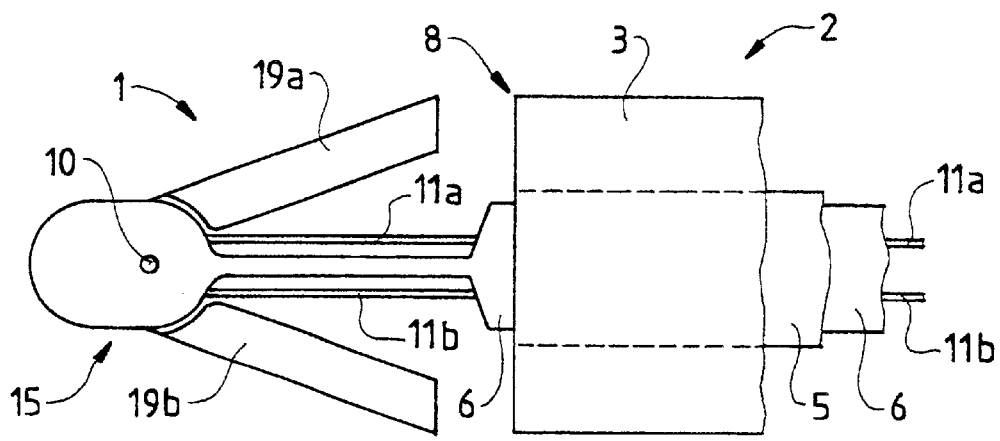
Figure 6:
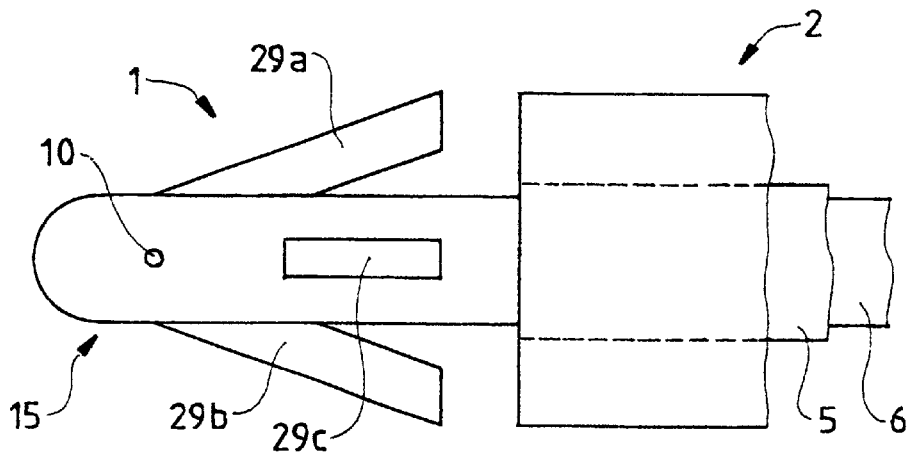
Figure 7:
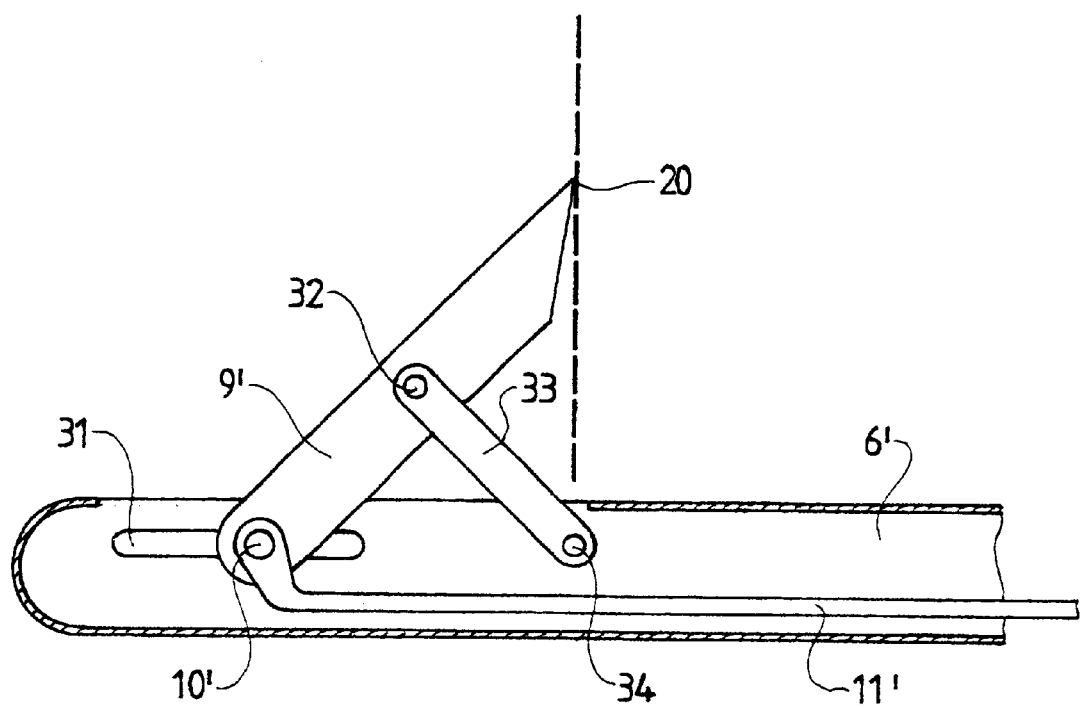

FIG. 1 is a sideview of a first embodiment mode of the fill bar of the invention in its functional position in an endoscope, FIG. 2 is a sideview of the distal zone of the fill bar of FIG. 1 with pivoted lever and shown in a partial sectional view of the endoscope, FIG. 3 is an enlarged section of the fill bar along line 3—3 in FIG. 1, FIG. 4 is a sideview of the distal zone of a fill bar of the invention shown in a second embodiment mode, FIG. 5 is a sideview of a fill bar of the invention shown in a third embodiment mode, FIG. 6 is a sideview of a fill bar of the invention of a fourth embodiment mode, and FIG. 7 is a sideview of the distal zone of a fill bar of the invention of a fifth embodiment mode.

A fill bar 1 is shown in highly schematic manner and in its functional position in an endoscope 2 in FIGS. 1 and 2. The endoscope 2 comprises a conventional outer shank tube 3 receiving an optics 4 which illustratively may be an illuminating and observing optics. The endoscope 2 is fitted furthermore with a transmission, i.e. a functional duct 5 running from proximal to distal. The fill bar 5 shall have been inserted into this duct 5 when it is in its functional position.

Essentially the fill bar 1 assumes the form of an elongated, cylindrical bar 6. At its distal, rounded tip area 15 projecting beyond the distal tip 8 of the endoscope 2, the fill bar 1 is fitted with a lever 9 which it supports in pivotable manner. In the shown embodiment mode, the lever 9 is linked in pivotable manner by its distal end 21 to a shaft 10 configured transversely to the longitudinal axis of the fill bar 1, as a result of which the lever 9 may pivot by its free lever end 20 away from the longitudinal axis of the fill bar 1.

To initiate and to control the pivoting of the lever 9, it is linked to a drive rod 11 running from the proximal side through the fill bar 1 containing a hollow cross-section 22 as far as the lever 9 where said rod acts in articulating manner on said lever above the pivot shaft 10 for instance in a borehole 13 in the lever 9. The drive rod 11 proximally projects beyond the proximal end 14 of the cylindrical bar 6 and the endoscope 2 and accordingly it may be manually actuated by the surgeon. When the rod 11 is shifted axially, it shall rest against the lever 9 above the pivot shaft 10 and as a result the translating motion of the actuation rod 11 is converted into a pivoting motion of the lever 9. When the actuation rod 11 illustratively is forced in the distal direction, the free end 20 of the lever 9 shall be pivoted away as shown in FIG. 2 by the arrows P1 and P2. On the other hand the lever 9 returns to the unpivoted state of FIG. 1 when the rod 2 is pulled in the proximal direction.

In order to move the fill bar 1 into its functional position, it shall first be shifted in the distal direction through the transmission duct 5 of the endoscope 2 until the distal region 15 of the fill bar 1 distally projects beyond the endoscope 2. Initially, in this process, the lever 9 is unpivoted from the lever 1 as shown in FIG. 1. Next the lever 9 may be pivoted from said lever by the above described axial shifting in the distal direction undergone by the actuation rod 11, as a result of which the cross-sectional area of the fill bar 1 in the region of the pivoted lever 9 is enlarged in the proximal direction.

When the fill bar 1 is in its functional position and the lever 9 has been pivoted away from it, the endoscope 2—now fitted with the rounding of its distal tip due to the fill bar 1—will be inserted into the body duct of a patient and be advanced as far as the anticipated field of surgery. Once the endoscope 2 has reached its anticipated position, the lever 9 is retracted on account of the proximally directed displacement of the actuation rod 11, whereby the fill bar 1—now being in its initial cross-section—can be moved again through the duct 5 of the endoscope 2. The fill bar 1 is removed in the proximal direction from the endoscope 2 and as a result the continuous duct 5 once more is clear and is hence available to insert an implement into the surgical region. Obviously the endoscope 2 remains in its anticipated position in the body duct after the fill bar has been removed.

Appropriately the actuation rod 11 for the lever 9 shall be locked relative to the fill bar 1 when the lever 9 has just assumed its desired position, whether it be pivoted away from the said bar or retracted toward it. Illustratively and schematically, such a locking element is indicated in FIG. 1 by a tightening screw 12 which enters a threaded borehole of the segment 14 of the cylindrical bar 6 proximally projecting beyond the endoscope 2, and which adequately clamps the actuation rod 11, whereby the lever 9 is affixed in the state that was just attained.

FIG. 2 shows that the free end 20 of the lever 9 is designed to rest against the distal end 8 of the endoscope 2. For that purpose it comprises at its proximal end face a beak 16 which may engage a substantially complementary recess 17 in the external peripheral surface of the distal tip 8 of the endoscope 2 when, following the lever 9 being pivoted away from the fill bar 1, this bar is pulled in the proximal direction. The beak 16 may be of arbitrary and for instance triangular or rounded geometry to facilitate its engagement of the recess 17 in the endoscope 2.

It is clear from the section of the fill bar 1 along line 3—3 of FIG. 1 shown in FIG. 3 that the lever 9 exhibits a cylindrically convex external surface 18 in order that the tissue of the body duct transmitting the endoscope 2 together with the fill bar 1 shall only come in contact with rounded surfaces. Moreover the hollow inner cross-section 22 of the fill bar 1 is shown, which makes it possible for the actuation rod 11 to run inside it in axially displaceable manner. This hollow cross-section 22 also may be selected in such manner that the actuation rod 11 shall be well guided laterally and cannot buckle transversely to the axial direction of actuation.

The illustrative embodiment of FIG. 4 differs from the fill bar 1 described heretofore in that proximally from a distal tip 7 the lever 9 is supported by the fill bar 1. Relative to FIG. 1, the shaft 10 therefore all has been shifted proximally. As a result the fill bar 1 retains a closed outer surface of its distal tip 7 even when the lever 9 has been pivoted away from it.

FIGS. 5 and 6 show fill bars of the invention with more than one pivotable lever. For instance FIG. 5 shows two levers which can pivot away from the fill bar 1 at opposite sides of it, both being linked at their distal ends to the same pivot shaft 10. Both levers are controlled from the proximal side in the manner already described above by means of an actuation rod 11a, 11b, that is being pivoted away from the fill bar 1 or being retracted toward it again, such actuation for instance being in individual or also in ganged manner.

Lastly FIG. 6 shows a fill bar 1 with four pivotable levers 29a–d that are mutually offset by 90° and rest on the fill bar 1. The lever configured on opposite sides of the fill bar 1 exhibit painwise the same length and an equal distance of their supporting shafts to the distal tip. In this manner the levers 29a and 29b are longer than the levers 29c and 29d, the latter being mounted on the far side of the fill bar 1 and hence not visible in the drawing.

As regards the embodiment modes shown so far, for instance that of FIG. 2, the lever 9 is pivoted by the actuation rod 11 which acts on the lever 9 at the support site 13 at a distance from the pivot shaft 10 of said lever. The result is a pivoting motion of the lever 9 about its pivot shaft 10, the free lever end 20 carrying out a circular motion about the pivot shaft 10.

In order that the lever 10 in the position of FIG. 2 shall be able to freely pivot in front of the distal end of the endoscope, that is of the shank tube 3, it must be initially advanced slightly distally. If then reliable support of the free lever end 20 at the shank tube 3 is desired, the bar 6 then must be slightly retracted proximally until the free end of the lever 9, as discussed in relation to FIG. 2, may come to rest against the shank tube 3. In order to collapse thereafter the lever 9, the bar 6 again must be advanced slightly in the distal direction in order that the lever be provided with the freedom of pivoting in from of the shank tube 3 which is necessary for collapsing it.

FIG. 7 shows an embodiment variation of the invention wherein the lever 9' can be unfolded and collapsed without the bar 6' requiring initial distal displacement.

In this design the lever 9' rests on a shaft 10' which also engages the actuation rod 11'. The shaft 10' in this embodiment mode however rests in longitudinally displaceable manner in an elongated slot 31 of the bar 6'. Moreover the lever 9' rests by a support 32 at a distance from the shaft 10' against a coupling lever 33 of which the other end rests in a support 34 on the bar 6'.

This design attains a kinematics whereby a longitudinal displacement of the actuation rod 11 shall pivot the lever 9' of which however the free end 20 moves transversely to the axis of the bar 6' along the dashed line.

Comparison with FIG. 2 shows that when the dashed line of FIG. 7 is situated exactly at the height of the front edge of the shank tube 3, the free end 20 of the lever 9' of FIG. 7 shall be pivoted precisely on the distal rim of the shank tube 3. When the lever 9' is pivoted out, the free end 20 will rest on the rim of the shank tube 3 where it can be supported. To pivot the lever 9' out and in, however, and contrary to the case of the embodiment of FIG. 2, it is no longer necessary to distally advance the fill bar 1 in order to attain free pivoting motion.

Obviously the invention is not restricted to the shown actuation mechanism for the lever(s). Instead the illustratively shown actuation rod 11 also may be replaced by alternative designs that shall implement the pivoting motion of the lever 9. For instance the lever also might be driven by a corresponding adjustment element. However in order to well sterilize and clean the fill bar, preferably the adjusting device shall be detachably affixed to the lever.

Even though security elements against axial shifting between endoscope and fill bar have been shown in no embodiment mode, such a device would be appropriate to preclude the fill bar from carrying out undesired axial motions relative to the endoscope. In its simplest design, such a device might again be for instance a simple clamping screw to tighten the fill bar in the endoscope. The clamping element illustratively might be detachable as above and be manually driven. Again elements of this kind or alternative ones are in the state of the art and are pertinently well known and therefore require no further discussion.

Moreover security elements may be used to assure that the fill bar in its functional position always shall assume a defined rotational position in the endoscope in order that the pivoted lever always cover in rounding manner the distal endoscope tip in the prescribed and simultaneously optimal way. This feature is especially advantageous when the transmission duct is mounted other than centrally symmetrically in the endoscope cross-section. Such elements for instance may be an axial groove at the proximal end in the inside wall of the endoscope transmission duct 5 into which shall be inserted a relevant pin at the fill bar. In this instance as well the expert also knows about alternative designs.

Furthermore the pivoting lever motion away from the fill bar might be facilitated by a spring that would be mounted between said pivoting lever and the cylindrical bar. At the same time said spring would support the lever in its spread-out state.

What is claimed is:

1. A fill bar (1) for an endoscope (2), comprising a device (9) which, in said bar's functional position, can change a cross-section of an end zone (15) distally projecting beyond a distal end (8) of the endoscope, the cross-section change being implemented from an adjustment system mounted proximally on the fill bar and through an adjustment link (11), wherein said device comprises a lever (9) that is pivotally configured on the distal end zone (15) of the fill bar (1) by its own distal end zone (21).

2. The fill bar (1) as claimed in claim 1, wherein the lever (9) is mounted proximally from a distal, rounded tip (7) of the fill bar (1).

3. The fill bar (1) as claimed in claim 1, wherein the lever (9) comprises a cylindrically convex external surface (18), said external surface being disposed relatively away from the fill bar (1).

4. The fill bar (1) as claimed in claim 2, wherein a free end (20) of the lever (9) is designed to rest against the distal end (8) of the endoscope (2).

5. The fill bar (1) as claimed in claim 1, wherein the adjusting system (11) is fitted with an affixation element (12).

6. The fill bar (1) as claimed in claim 1, wherein several levers (19a–b, 29a–d) that may spread out in different directions are disposed at the distal end zone (15) of the fill bar (1).

7. The fill bar (1) as claimed in claim 6, wherein each of the several levers (29a–d) has different lengths.

8. The fill bar (1) as claimed in claim 1, wherein the adjustment link (11) is designed such that a free end (20) of the lever (9) moves along a straight path perpendicularly to a longitudinal axis of the fill bar when the lever is displaced by driving the adjustment link (11', 10', 31, 33).

* * * * *